US006395729B1

(12) United States Patent
Ferzaz et al.

(10) Patent No.: US 6,395,729 B1
(45) Date of Patent: May 28, 2002

(54) USE OF PYRIDAZINO[4,5-B]INDOLE-1-ACETAMIDE DERIVATIVES FOR PREPARING MEDICINES FOR TREATING DISEASES RELATED TO THE DYSFUNCTION OF PERIPHERAL BENZODIAZEPIN RECEPTORS

(75) Inventors: Badia Ferzaz, Antony; Jésus Benavides, Chatenay-Malabry; Frank Marguet, Verrieres le Buisson; Jacques Froissant, Moree; Benoît Marabout, Chilly Mazarin; Yannick Evanno; Mireille Sevrin, both of Paris; Phikip Janiak, Gif-sur-Yvette, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/889,983

(22) PCT Filed: Jan. 21, 2000

(86) PCT No.: PCT/FR00/00135
§ 371 (c)(1),
(2), (4) Date: Jul. 25, 2001

(87) PCT Pub. No.: WO00/44384
PCT Pub. Date: Aug. 3, 2000

(30) Foreign Application Priority Data
Jan. 26, 1999 (FR) .......................................... 99 00806

(51) Int. Cl.⁷ ................................................. A61K 31/55
(52) U.S. Cl. ....................................................... 514/220
(58) Field of Search ......................................... 514/220

(56) References Cited

FOREIGN PATENT DOCUMENTS

| DE | 31 21 137 | 12/1982 |
| GB | 2 290 292 | 12/1995 |
| WO | 98/15552 | 4/1998 |
| WO | 99/06406 | 2/1999 |

OTHER PUBLICATIONS

Derwent Abstract (1999)–153682.

Derwent Abstract (1998)–240772.

Derwent Abstract (1982)–09422J.

Primary Examiner—Raymond Henley, III
(74) Attorney, Agent, or Firm—Paul E. Dupont; Michael D. Alexander

(57) ABSTRACT

Pyridazino[4,5-b]indole-1-acetamide derivatives for the prevention or treatment of diseases linked to the dysfunctioning of peripheral-type benzodiazepine receptors.

13 Claims, No Drawings

USE OF PYRIDAZINO[4,5-B]INDOLE-1-ACETAMIDE DERIVATIVES FOR PREPARING MEDICINES FOR TREATING DISEASES RELATED TO THE DYSFUNCTION OF PERIPHERAL BENZODIAZEPIN RECEPTORS

This is a 371 of PCT/FR00/00135 filed Jan. 21, 2000.

Use of pyridazino[4,5-b]indole-1-acetamide derivatives for the preparation of medicaments for diseases linked to the dysfunctioning of peripheral-type benzodiazepine receptors.

In the context of the search for compounds which can promote the regeneration of the axons of the peripheral nerve cells after lesion, there has been identified, among the compounds of international patent application PCT/FR98/01667, a subclass of compounds of general formula (I)

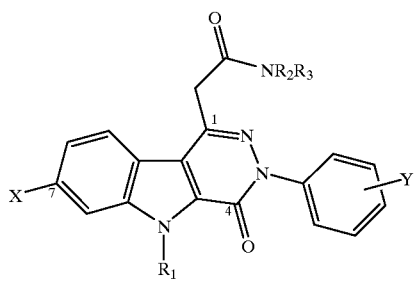

in which

X represents a halogen atom,

Y represents one or more atoms or groups chosen from hydrogen, halogens and hydroxyl, methyl, methoxy and nitro groups, $R_1$ represents a $(C_1-C_4)$alkyl group, $R_2$ and $R_3$ each represent, independently of each other, a hydrogen atom or a $(C_1-C_4)$alkyl group, or alternatively $R_2$ and $R_3$ form, with the nitrogen atom carrying them, a pyrrolidinyl, piperidinyl or morpholinyl group.

These compounds possess a high affinity for the peripheral-type benzodiazepine receptors (p sites, or PBR), and some induce, in particular, a reduction in neuronal loss in the facial nucleus after cutting of the facial nerve. They also have cardio- and renoprotective effects.

A particularly advantageous compound for use according to the invention is, for example, 7-chloro-N,N,5-trimethyl-4-oxo-3-phenyl-3,5-dihydro-4H-pyridazino[4,5-b]indole-1-acetamide.

The latter may be prepared according to the following procedure, given by way of example.

EXAMPLE
(Compound No. 1 of the Table Which Follows)

1. Ethyl 6-chloro-1-methyl-1H-indole-2-carboxylate

A suspension of 1.8 g (45 mmol) of sodium hydride at 60% (previously washed with petroleum ether) and of 8.0 g (35.8 mmol) of ethyl 6-chloro-1H-indole-2-carboxylate in 80 ml of N,N-dimethylformamide is stirred for 2 h at room temperature; 2.8 ml (45 mmol) of iodomethane are then added and the mixture is stirred at room temperature for 4 h.

5 ml of absolute ethanol are added and the solvent is evaporated under reduced pressure. The residue is taken up in water and the mixture is extracted with dichloromethane, the organic phase is dried, filtered, the solvent evaporated under reduced pressure and the residue purified by chromatography on a silica gel column.

8.5 g (35.7 mmol) of a white crystalline compound are isolated.

Melting point: 75.5–76.5° C.

2. Ethyl 6-chloro-2-(ethoxycarbonyl)-1-methyl-oxo-1H-indole-3-acetate 4 ml (36.4 mmol) of titanium tetrachloride are added to a solution of 4 ml (36 mmol) of ethyl chlorooxoacetate in 100 ml of 1,2-dichloroethane. The reaction mixture is stirred for 30 min at room temperature, and then 7.8 g (32.8 mmol) of ethyl 6-chloro-1-methyl-1H-indole-2-carboxylate are added and the reaction mixture is stirred for 4 h at room temperature.

The medium is cooled and 200 ml of dichloromethane and 100 ml of water are added. The organic phase is decanted off, it is washed with water, dried over sodium sulphate, filtered, the filtrate concentrated under reduced pressure and the residue purified by chromatography on a silica gel column.

9.4 g (29.0 mmol) of product are isolated.

Melting point: 94–95° C.

3. Ethyl 7-chloro-5-methyl-4-oxo-3-penyl-3,5-dihydro-4H-pyridazino[4,5-b]indole-1-carboxylate 4 ml (40.6 mmol) of phenylhydrazine are added, at room temperature, to a solution of 4.6 g (13.6 mmol) of ethyl 6-chloro-2-(ethoxycarbonyl)-1-methyl-oxo-1H-indole-3-acetate in 120 ml of acetic acid. The reaction mixture is stirred for 30 min at room temperature and then for 4 h under reflux. The medium is cooled and 350 ml of dichloromethane and 100 ml of water are added. The organic phase is decanted off, washed with a saturated aqueous sodium hydrogen carbonate solution, then with water, dried over sodium sulphate, filtered, concentrated under reduced pressure and the residue purified by chromatography on a silica gel column.

4.1 g (10.7 mmol) of product are isolated.

Melting point: 216–218.5° C.

4. 7-Chloro-1-(hydroxymethyl)-5-methyl-3-phenyl-3,5-dihydro-4H-pyridazino[4,5-b]indol-4-one 2.5 g (66.1 mmol) of sodium borohydride are added to a solution of 4.04 g (10.6 mmol) of ethyl 7-chloro-5-methyl-4-oxo-3-phenyl-3,5-dihydro-4H-pyridazino[4,5-b]indole-1-carboxylate in 150 ml of tetrahydrofuran. 2.25 ml of methanol are then gradually added, with stirring, and then the mixture is heated under reflux for 5 h.

The mixture is poured over an ice-cold 1 M hydrochloric acid solution and an insoluble matter is isolated by filtration on sintered glass, washed with water and with diethyl ether and then dried.

3.3 g (9.7 mmol) of compound are isolated in the form of a white solid which is used as it is in the next step.

Melting point: 219–220.5° C.

5. 7-Chloro-5-methyl-4-oxo-3-phenyl-3,5-dihydro-4H-pyridazino[4,5-b]indole-1-carboxaldehyde 5.7 g (65.6 mmol) of manganese dioxide are added to a solution of 3.3 g (9.7 mmol) of 7-chloro-1-(hydroxymethyl)-5-methyl-3-phenyl-3,5-dihydro-4H-pyridazino[4,5-b]indol-4-one in 300 ml of dichloromethane and the reaction mixture is stirred for 24 h under reflux.

3

The medium is cooled, filtered on a Teflon™ membrane and the solid is rinsed with dichloromethane and then the filtrate is concentrated under reduced pressure.

2.88 g (8.53 mmol) of compound are isolated in the form of a white solid which is used as it is in the next step.

Melting point: 235–236° C.

6. 7-Chloro-5-methyl-4-oxo-3-phenyl-3,5-dihydro-4H-pyridazino[4,5-b]indole-1-acetonitrile 1.27 g (10.96 mmol) of potassium 1,1-dimethylethoxide are added, in small portions, to a solution of 2.14 g (10.96 mmol) of 1-[(isocyanomethyl)-sulphonyl]-4-methylbenzene in 50 ml of 1,2-dimethoxyethane, the reaction mixture is stirred for 30 min at −60° C., 2.88 g (8.53 mmol) of 7-chloro-5-methyl-4-oxo-3-phenyl-3,5-dihydro-4H-pyridazino[4,5-b]indole-1-carboxaldehyde are added and the reaction mixture is stirred for 3 h 30 min at −60° C. 9 ml of methanol are added and the reaction mixture is again stirred for 30 min at room temperature and for 1 h under reflux.

The medium is cooled, concentrated under reduced pressure, water, 5 ml of acetic acid and 200 ml of dichloromethane are added to the residue, the organic phase is decanted off and the aqueous phase is extracted with dichloromethane. The organic phases are combined, washed with water, dried over sodium sulphate, filtered, concentrated under reduced pressure and the residue is purified by chromatography on silica gel. 1.87 g (5.36 mmol) of compound are isolated in the form of a white solid which is used as it is in the next step.

Melting point: 305–315° C.

7. Methyl 7-chloro-5-methyl-4-oxo-3-phenyl-3,5-dihydro-4H-pyridazino[4,5-b]indole-1-acetate Hydrogen chloride is added to a solution of 1.83 g (5.25 mmol) of 7-chloro-5-methyl-4-oxo-3-phenyl-3,5-dihydro-4H-pyridazino[4,5-b]indole-1-acetonitrile in 250 ml of methanol until the solution is saturated and the reaction mixture is stirred for 4 h under reflux.

The medium is cooled, the reaction mixture concentrated under reduced pressure and 25 ml of water and 25 ml of methanol are added to the residue. After stirring, the insoluble matter is recovered by filtration, washed with water and with diethyl ether, dried and purified by chromatography on a silica gel column.

1.00 g (2.62 mmol) of compound is isolated in the form of a white solid.

Melting point: 188.5–190° C.

8. 7-Chloro-N,N,5-trimethyl-4-oxo-3-phenyl-3,5-dihydro-4H-pyridazino[4,5-b]indole-1-acetamide 3 ml (6 mmol) of trimethylaluminium (2 M in toluene) are added, at 0° C., under argon, to a solution of 0.49 g (6 mmol) of dimethylamine hydrochloride in 80 ml of toluene and the reaction mixture is stirred for 1 h 30 min at room temperature.

0.21 g (0.55 mmol) of methyl 7-chloro-5-methyl-4-oxo-3-phenyl-3,5-dihydro-4H-pyridazino-[4,5-b]indole-1-acetate is added and the reaction mixture is stirred for 6 h under reflux.

The medium is cooled to 4° C., 10 ml of water and 100 ml of dichloromethane are added, the solution is filtered and the filtrate is concentrated under reduced pressure.

Water, 1 M hydrochloric acid and 150 ml of dichloromethane are added to the residue, the organic phase is separated, washed with water, dried over sodium sulphate, filtered, concentrated under reduced pressure and the residue is purified by chromatography on a silica gel column.

After recrystallization from a mixture of dichloromethane and ethyl acetate, 0.2 g (0.51 mmol) of compound is isolated in the form of a white solid with a cottony appearance.

Melting point: 229.5–230° C.

The table which follows illustrates the chemical structures and physical properties of some compounds which can be used according to the invention.

Legend to the Table

"Me" and "Et" designate a methyl and ethyl group, respectively.

"pyrrolid", "piperid" and "morph" designate a pyrrolidinyl, piperidinyl and morpholinyl group, respectively.

TABLE

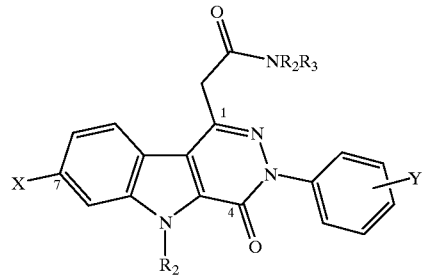

(I)

| No. | X | Y | $R_1$ | $NR_2R_3$ | m.p. (° C.) |
|---|---|---|---|---|---|
| 1 | Cl | H | Me | $NMe_2$ | 229.5–230 |
| 2 | Cl | H | Me | $NEt_2$ | 167–168 |
| 3 | Cl | H | Me | pyrrolid | 260–263 |
| 4 | Cl | H | Me | morph | 273.5–274.5 |
| 5 | Cl | 3-Me | Me | $NMe_2$ | 204–205.5 |
| 6 | Cl | 3-Me | Me | $NEt_2$ | 200.5–201 |
| 7 | Cl | 3-Me | Me | pyrrolid | 268–269.5 |
| 8 | Cl | 3-Cl | Me | $NMe_2$ | 231–232 |
| 9 | Cl | 3-Cl | Me | $NEt_2$ | 202.5–203 |
| 10 | Cl | 3-Cl | Me | pyrrolid | 257–258.5 |
| 11 | Cl | 3-Cl | Me | piperid | 218–219 |
| 12 | Cl | 2-Cl | Me | $NMe_2$ | 253–255 |
| 13 | Cl | 2-Cl | Me | $NEt_2$ | 206–208 |
| 14 | Cl | 2-Cl | Me | pyrrolid | 295–297 |
| 15 | Cl | 4-Cl | Me | $NMe_2$ | 235–237 |
| 16 | Cl | 4-Cl | Me | $NEt_2$ | 223.5–224.5 |
| 17 | Cl | 4-Cl | Me | pyrrolid | 265–266 |
| 18 | Cl | 3-OMe | Me | $NMe_2$ | 200.5–202.5 |
| 19 | Cl | 3-OMe | Me | $NEt_2$ | 201–202 |
| 20 | Cl | 3-OMe | Me | pyrrolid | 240–242 |
| 21 | Cl | $3-NO_2$ | Me | $NMe_2$ | 275–277.5 |
| 22 | CJ | $3-NO_2$ | Me | $NEt_2$ | 228–228.5 |
| 23 | Cl | $3-NO_2$ | Me | pyrrolid | 261–263 |
| 24 | Cl | 3-F | Me | $NMe_2$ | 225–226.5 |
| 25 | Cl | 3-F | Me | $NEt_2$ | 171–172 |
| 26 | Cl | 3-F | Me | pyrrolid | 270–271.5 |
| 27 | Cl | $3,5-(Cl)_2$ | Me | $NEt_2$ | 239–240.5 |
| 28 | Cl | 4-Cl | Me | NMeEt | 216.5–217.5 |
| 29 | Cl | H | Me | NHMe | 305–307 |
| 30 | Cl | H | Me | $NH_2$ | 292–293 |
| 31 | Cl | 4-OMe | Me | $NMe_2$ | 233–234 |
| 32 | Cl | 4-OMe | Me | $NEt_2$ | 172–174 |
| 33 | Cl | 4-OH | Me | $NMe_2$ | 298–300 |
| 34 | Cl | 4-OH | Me | $NEt_2$ | 271–272 |

The protocols and the results of the trials have been carried out are described below.

Study of the [$^3$H]Ro5-4864 Binding to the Peripheral-type Benzodiazepine Receptors The affinity of the compounds of the invention for peripheral-type benzodiazepine receptors (p site, or PBR) was determined.

The p sites receptors can be selectively labelled in rat kidney membranes incubated in the presence of [$^3$H]Ro5-4864. The compounds were the subject of a study in vitro with respect to their affinity for these receptors. The animals used are 180 to 300 mg male Sprague-Dawley rats (Iffa Credo). After decapitation, the kidney is removed and the tissue is homogenized at 4° C. by means of a Polytron™ homogenizer for 2 min at 6/10 of the maximum speed in 35 volumes of 50 mM phosphate $Na_2HPO_4$ buffer at a pH adjusted to 7.5 with $NaH_2PO_4$. The membrane homogenate is filtered on gauze and diluted 10-fold with buffer.

[$^3$H]Ro5-4864 (specific activity: 70–90 Ci/mmol; New England Nuclear), at a concentration of 0.5 nM, is incubated in the presence of 100 1 of membrane homogenate in a final volume of 1 ml of buffer containing the test compound.

After a 3-h incubation at 0° C., the membranes are recovered by filtration on Whatman GF/B™ filters which are washed with twice 4.5 ml of cold incubation buffer (0° C.). The quantity of radioactivity retained by the filter is measured by liquid scintigraphy.

For each concentration of compound studied, the percentage inhibition of the binding of [$^3$H]Ro5-4864, and then the concentration $IC_{50}$, concentration which inhibits 50% of the specific binding, are determined.

The $IC_{50}$ values for the most active compounds range from 0.6 nM to 20 nM.

The compounds which may be used according to the invention are consequently ligands with high affinity for the peripheral-type benzoiazepine receptors.

Study of the Neurotrophic Activity

Test of regeneration of the lesioned facial nerve by measuring the functional recovery of the palpebral reflex, according to a modification of the method of K. Kujawa et al., *Experimental Neurology* (1989) 105 80–85.

Lesion of the facial nerve by local freezing causes degeneration of the distal part of the facial nerve and a loss of the blinking function of the eyelid. The products to be studied are administered by the intraperitoneal or oral route twice per day at an interval of 6 to 8 h, daily for 10 days (duration of the experiment). The first treatment is administered 30 min before the lesion.

Monitoring of the animals: the recovery of the function of the eyelids in the lesioned animals is monitored daily, once in the morning from D0 to D5 and twice (morning and evening at an interval of 6 to 8 h) from D6 to D10, before each treatment, according to a theoretical score ranging from 0 to 4.

Score 0: eye open, score 1: eye closed with a degree less than half of the eye; score 2: degree of closure between ½ and ¾; score 3: degree of closure greater than ¾; score 4: eye completely closed.

The results are expressed by the ratio of the AUC (area under the curve) values for the treated group and the control group. The AUC ratios for the most active compounds are between 1.12 and 1.20.

These compounds therefore increase by 12 to 20% the recovery of the palpebral reflex after lesion of the facial nerve.

Test of Survival of the Motoneurons After Cutting of the Facial Nerve in 4-day-old Rats After lesioning of the facial nerve in immature rats, the motoneurons of the facial nucleus undergo neuronal death by apoptosis. The evaluation of neuronal survival is carried out using histological and neuronal counting methods.

4-Day-old immature rats are anaesthetized with pentobarbital (3 mg/kg by the i.p. route). The right facial nerve is exposed and cut, where it leaves the stylomastoid foramen. After regaining consciousness, the young rats are returned to their mothers and treated, for 7 d, by one or two daily administrations, by the oral or intraperitoneal route, at doses ranging from 1 to 10 mg/kg. 7 d after the lesioning, the animals are decapitated and the brains frozen in isopentane at −40° C. The facial nucleus is cut using a cryostat, into 10 $\mu$m sections, in its entirety. The motoneurons are stained with cresyl violet and counted with the aid of the Histo™ software (Biocom™).

In this model, the most active compounds increase neuronal survival by about 10 to 30%. By way of example, the compound described in the Example (No. 1 of the table) increases neuronal survival by 31% by the i.p. route.

The results of the above-described trials show that the compounds of general formula (I) promote nerve regeneration.

Study of the Cardioprotective Effects

The cardioprotective effects were studied on hearts isolated from rabbits subjected to a regional ischaemia and to a reinfusion. The size of infarction as well as the recovery of the contractile function upon reinfusion were measured.

New Zealand rabbits (2.3 to 2.5 kg, ESD France) are anaesthetized with a ketamine-xylasine mixture and heparinized. The heart is removed and rapidly infused by the retrograde aortic route at a pressure of 75 mmHg with a Krebs Henselheit-type solution. A balloon is introduced into the left ventricle and a telediastolic pressure of 5 mmHg is applied. After a stabilizing period of 20 min, the compound to be studied (1 mM) or the vehicle is added to the infusion solution 15 min before the ischaemia and during the entire duration of the experiment. The regional ischaemia is created by complete ligation of the left coronary artery for 30 min, the heart then being reinfused for 2 h.

The ventricular pressure, heart rate and coronary output parameters are monitored during the whole experiment.

After the reinfusion, the coronary artery is again occluded and China ink is infused in order to delimit the area at risk. Transverse sections are then prepared and incubated in a 1% triphenyltetrazolium solution so as to measure the size of the infarction. The quantification of the necrosed area, expressed as % of the area at risk, is obtained by means of image-analysing software.

By way of example, the compound described in the Example (No. 1 of the table) brings about a significant reduction in the size of the infarction of 47% (controls: 41.7±5.3 vs compound studied: 22±3.3; p<0.01). The areas with a risk of about 50% are comparable in both groups.

Compound No. 1 reduces the contracture during reinfusion and significantly restores the left ventricular pressure (percentage of preischaemic recovery of 36% after 2 h of reinfusion in the controls against 65% in the treated animals), the maximum and minimum dP/dt values and the double frequency-pressure product.

Study of the Renoprotective Effects

The experiment is carried out on Sprague-Dawley male rats (Charles River France) of 270 to 330 g. The animals are anaesthetized with pentobarbital (60 mg/kg i.p.), intubated and artificially ventilated, their temperature is maintained between 37 and 38° C.

A 3 cm laparotomy is performed on the animal in dorsal decubitus, the right and left renal arteries are exposed and occluded for 30 min, and then the kidneys are reinfused under visual monitoring and the incision is closed. The serum creatinine and urea nitrogen levels are determined from blood samples collected in the orbital sinus, at D0 (before anaesthesia), and then at D1, D2, D3, D4, D8 (after 1 occlusion-reinfusion).

The compound to be studied, or its vehicle (Tween 80 at 2%) is administered at the dose of 3 mg/kg by the i.p. route 60 min before the occlusion.

By way of example, compound No. 1 reduces creatininaemia by 56% and uraemia by 49%, compared with the vehicle at D3. It also reduces the mortality in the animals: $\frac{1}{12}$ against $\frac{4}{9}$ in the animals which received only the vehicle.

The preceding two trials show, on the one hand, that the compounds which can be used according to the invention reduce the size of the infarction induced by cardiac ischaemia-reinfusion in rabbits and allows better recovery of the contractile function upon reinfusion, and, on the other hand, that they limit the acute renal insufficiency caused by a renal ischaemia-reinfusion episode.

The compounds of general formula (I) can therefore be used for the preparation of medicaments for the prevention and treatment of peripheral neuropathies of different types, such as trauma-related or ischaemic neuropathies, infectious, alcohol-related, drug-related or genetic neuropathies, as well as motoneuron conditions such as spinal amyotrophies and amyotrophic lateral sclerosis. These medicaments also find application in the treatment of neurodegenerative diseases of the central nervous system, either of the acute type such as cerebrovascular accidents and cranial and medullary traumas, or of the chronic type such as autoimmune diseases (multiple sclerosis), Alzheimer's disease, Parkinson's disease and any other disease in which the administration of neurotrophic factors is expected to have a therapeutic effect.

The compounds which can be used according to the invention may also be used in the treatments of acute or chronic renal insufficiency, glomerulonephritis, diabetic nephropathy, cardiac ischaemia and insufficiency, myocardial infarction, ischaemia of the lower limbs, coronary vasospasm, angina pectoris, pathological conditions associated with the cardiac valves, inflammatory cardiac diseases, side effects due to cardiotoxic medicaments or to the aftereffects of cardiac surgery, atherosclerosis and its thromboembolic complications, restenosis, graft rejections, conditions linked to incorrect proliferation or migration of the smooth muscle cells.

Moreover, recent literature data indicates that the peripheral-type benzodiazepine receptor could play a fundamental role in regulating cell proliferation and cancerization processes. In general, and in comparison with normal tissues, an increased density of peripheral-type benzodiazepine receptors is observed in various types of tumour and cancer.

In human astocytomas, the level of expression of the peripheral-type benzodiazepine receptor is correlated with the degree of malignancy of the tumour, the proliferation index and the survival of the patients. In human cerebral tumours, the increase in the number of peripheral-type benzodiazepine receptors is used as a diagnostic indication in medical imaging and as a therapeutic target for conjugates consisting of a ligand for the peripheral-type benzodiazepine receptor and a cytostatic drug. A high density of peripheral-type benzodiazepine receptors is also observed in ovarian carcinomas and breast cancers. As regards the latter, it has been demonstrated that the level of expression of the peripheral-type benzodiazepine receptors is linked to the aggressive potential of the tumour; furthermore, the presence of an agonist of the peripheral-type benzodiazepine receptor stimulates the growth of a mammary cancer line.

All these results, which suggest a deleterious function of the peripheral-type benzodiazepine receptor in cancerization processes, constitute a pertinent basis for the search for synthetic ligands specific for the peripheral-type benzodiazepine receptor which are capable of blocking the effects thereof.

The compounds may therefore be used for the treatment of tumours and cancers.

The peripheral-type benzodiazepine receptors are also present in the skin and, by virtue of these, the compounds which can be used according to the invention may be used for the prophylaxis or the treatment of cutaneous stresses.

The expression cutaneous stress is understood to mean the various situations which could cause damage in particular in the epidermis, regardless of the agent causing this stress. This agent may be inside and/or outside the body, such as a chemical or free-radical agent, or else outside, such as ultraviolet radiation.

Thus, the compounds which can be used according to the invention are intended for preventing and/or combating cutaneous irritations, dartres, erythemas, dysaesthetic sensations, sensations of overheating, pruritus of the skin and/or of the mucous membranes, ageing and may also be used in skin disorders such as, for example, psoriasis, pruriginous diseases, herpes, photodermatosis, atopic dermatitis, contact dermatitis, lichens, prurigo, pruritus, insect bites, fibrosis and other collagen maturation disorders, in immunological disorders or else in dermatological conditions such as eczema.

Thus, the subject of the present invention is the use of the compounds of general formula (I) for the preparation of pharmaceutical compositions containing an effective dose of at least one compound of general formula (I), in the form of a pharmaceutically acceptable base, salt or solvate, and as a mixture, where appropriate, with suitable excipients.

The said excipients are chosen according to the pharmaceutical dosage form and the desired mode of administration.

The pharmaceutical compositions according to the invention may thus be intended for oral, sublingual, subcutaneous, intramuscular, intravenous, topical, intratracheal, intranasal, transdermal, rectal or intraocular administration.

The unit forms for administration may be, for example, tablets, gelatin capsules, granules, powders, oral or injectable solutions or suspensions, transdermal patches or suppositories. For topical administration, ointments, lotions and collyria may be envisaged.

The said unit forms are in doses which allow a daily administration of 0.001 to 20 mg of active ingredient per kg of body weight, depending on the galenic form.

To prepare tablets, there are added to the active ingredient, micronized or otherwise, a pharmaceutical vehicle which may be composed of diluents, such as for example lactose, microcrystalline cellulose, starch, and formulation adjuvants such as binders, (polyvinylpyrrolidone, hydroxypropyl methyl cellulose, and the like), glidants such as silica, lubricants such as magnesium stearate, stearic acid, glyceryl tribehenate, sodium stearylfumarate. Wetting agents or surfactants such as sodium lauryl sulphate may also be added.

The techniques for implementation may be direct compression, dry granulation, wet granulation, or hot melting.

The tablets may be uncoated, sugar-coated, for example with sucrose, coated with various polymers or other appropriate materials. It may be designed to allow rapid, delayed or prolonged release of the active ingredient by virtue of polymeric matrices or of specific polymers used in the coating.

To prepare gelatin capsules, the active ingredient is mixed with dry (simple mixing, dry or wet granulation, or hot melting), liquid or semisolid pharmaceutical vehicles.

The gelatin capsules may be hard or soft, film-coated or otherwise, so as to have a rapid, prolonged or delayed activity (for example for an enteric form).

A composition in the form of a syrup or an elixir or for administration in the form of drops may contain the active ingredient together with a sweetener, preferably calorie-free, methylparaben or propylparaben as antiseptic, a flavour modifier and a colouring agent.

The powders and granules which are dispersible in water may contain the active ingredient in the form of a mixture with dispersing agents or wetting agents, or dispersing agents such as polyvinylpyrrolidone, as well with sweeteners and taste-enhancing agents.

For rectal administration, suppositories are used which are prepared with binders melting at the rectal temperature, for example cocoa butter or polyethylene glycols.

For parenteral administration, aqueous suspensions, isotonic saline solutions or sterile solutions which are injectable are used which contain pharmacologically compatible dispersing agents and/or wetting agents, for example propylene glycol or butylene glycol.

The active ingredient may also be formulated in the form of microcapsules, optionally with one or more carriers or additives, or else with a polymeric matrix or with a cyclodextrin (transdermal patches, prolonged-release forms).

The topical compositions according to the invention comprise a medium compatible with the skin. They may be provided in particular in the form of aqueous, alcoholic or aqueous-alcoholic solutions, gels, water-in-oil or oil-in-water emulsions having the appearance of a cream or a gel, microemulsions, aerosols, or else in the form of vesicular dispersions containing ionic and/or nonionic lipids. These galenic forms are prepared according to the customary methods in the fields considered.

Finally, the pharmaceutical compositions according to the invention may contain, apart from a compound of general formula (I), other active ingredients which may be useful in the treatment of the disorders and diseases indicated above.

What is claimed is:

1. A method for the prevention or treatment of diseases and disorders linked to the dysfunctioning of peripheral-type benzodiazepine receptors which comprises administering to a patient in need thereof a compound of formula (I)

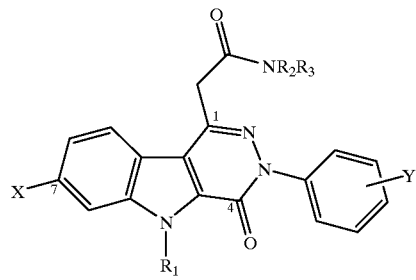

wherein
X is halogen,
Y is hydrogen or one or more substituents selected from hydrogen, halogen, hydroxyl, methyl, methoxy and nitro,
$R_1$ is $(C_1-C_4)$alkyl,
$R_2$ and $R_3$ are independently hydrogen or $(C_1-C_4)$alkyl, or $R_2$ and $R_3$ together with the nitrogen atom to which they are attached represent a pyrrolidinyl, piperidinyl or morpholinyl group.

2. A method according to claim 1 wherein in the compound of formula (I) X is chloro and $R_1$ is methyl.

3. A method according to claim 1 wherein the disease or disorder is a degenerative disease of the central or peripheral nervous system.

4. A method according to claim 1 wherein the disease or disorder is a cardiac disease or disorder.

5. A method according to claim 1 wherein the disease or disorder is a nephropathy.

6. A method according to claim 1 wherein the disease or disorder is a cutaneous stress.

7. A method according to claim 1 wherein the disease or disorder is a tumour or a cancer.

8. A method according to claim 2 wherein the compound of formula (I) is 7-chloro-N,N,5-trimethyl-4-oxo-3-phenyl-3,5-dihydro-4H-pyridazino[4,5-b]indole-1-acetamide.

9. A method according to claim 8 wherein the disease or disorder is a degenerative disease of the central or peripheral nervous system.

10. A method according to claim 8 wherein the disease or disorder is a cardiac disease or disorder.

11. A method according to claim 8 wherein the disease or disorder is a nephropathy.

12. A method according to claim 8 wherein the disease or disorder is a cutaneous stress.

13. A method according to claim 8 wherein the disease or disorder is a tumour or a cancer.

* * * * *